US006498492B1

(12) United States Patent
Rezvani

(10) Patent No.: US 6,498,492 B1
(45) Date of Patent: Dec. 24, 2002

(54) PROCESS OF MEASURING CONDUCTIVITY USING A PH ANALYZER

(75) Inventor: Behzad Rezvani, Anaheim, CA (US)

(73) Assignee: Rosemount Analytical Inc., Irvine, CA (US)

( * ) Notice: Subject to any disclaimer, the term of this patent is extended or adjusted under 35 U.S.C. 154(b) by 12 days.

(21) Appl. No.: 09/817,598

(22) Filed: Mar. 23, 2001

(51) Int. Cl.[7] .................................... G01N 27/46

(52) U.S. Cl. .................................... 324/438; 324/439

(58) Field of Search .................................... 324/438, 439, 324/444; 436/149; 422/82.01

(56) References Cited

U.S. PATENT DOCUMENTS 4,751,466 A * 6/1988 Colvin et al. ............... 324/444
5,152,882 A 10/1992 Benton ....................... 204/416
5,469,070 A 11/1995 Koluvek ..................... 324/713
5,621,669 A 4/1997 Bjornsson .............. 364/571.01

* cited by examiner

*Primary Examiner*—Gregory Toatley
(74) *Attorney, Agent, or Firm*—Westman, Champlin & Kelly, P.A.

(57) ABSTRACT

A pH analyzer is operated to measure conductivity of a solution by applying a substantially DC current having peak values, $I_{REF-PEAK}$, to a reference electrode of an ion-sensitive sensor having an ion-specific electrode in contact with the solution. The reference electrode is coupled to the ion-specific electrode through the solution. The peak voltage, $V_{ION-PEAK}$, between the ion-specific electrode and the common electrode is measured, and the conductivity of the solution is identified based on $$C_{SOL} = \frac{I_{REF-PEAK}}{V_{ION-PEAK}}.$$

20 Claims, 1 Drawing Sheet

PROCESS OF MEASURING CONDUCTIVITY USING A PH ANALYZER

FIELD OF THE INVENTION

This invention relates to conductivity measurement, and particularly to a process of measuring conductivity of a fluid using a pH analyzer.

BACKGROUND OF THE INVENTION

Conductivity measuring analyzers are well known in the art and are used to measure the conductivity of a fluid, such as a liquid or dispersion of solids in a liquid. Conductivity analyzers are used to investigate the properties of electrolyte solutions, such as the degree of disassociation, the formation of chemical complexes and hydrolysis. A contact conductivity sensor employs a pair of electrodes in contact with the electrolyte solution. The measurement circuit supplies a voltage to the electrodes that such that the resulting current between the electrodes is used to measure conductivity. More specifically, the sensor provides an output current that is a measurement of the conductivity of the solution, which is the inverse of resistivity.

In many industrial process control systems, it is necessary to measure both the conductivity of a solution, as well as its pH. Ordinarily, an ion-sensitive sensor, such as a pH sensor, and a separate conductivity sensor, are employed in the process control system. In some cases, however, a conductivity sensor is simply not available. For example, certain maintenance and diagnostic operations may require conductivity measurements that might not be needed in normal operation of the process control system. In other cases, the ion-sensitive sensor and conductivity sensor might not share the same measurement circuit, and may require separate electrical control loops, which can be expensive and difficult to retrofit into existing systems. The present invention is directed to the problem of measuring conductivity of a fluid in the absence of a conductivity sensor, and particularly to a method of operating an ion-sensitive sensor to measure conductivity of a fluid, so that the analyzer may be operated as both a pH analyzer and a conductivity analyzer.

SUMMARY OF THE INVENTION

According to the present invention, an analyzer is operated to measure conductivity of a solution. A current, $I_{REF}$, is applied to the reference electrode of an ion-sensitive sensor having an ion-specific electrode. The current is a substantially constant current having first and second opposite states of substantially equal value. A peak-to-peak voltage, $V_{ION}$, between the ion-specific electrode and a common electrode is measured, and the conductivity of the solution, $C_{SOL}$, is identified based on $$C_{SOL} = \frac{I_{REF}}{V_{ION}}.$$

According to another aspect of the present invention, the analyzer operates the ion-sensitive sensor to measure pH of the sample solution and operates the ion-sensitive sensor to measure conductivity of the solution. More particularly, an average voltage, $V_{ION-AVE}$, is measured between the ion-specific electrode and the common electrode and an average voltage, $V_{REF-AVE}$, is measured between the reference electrode and the common electrode. The pH of the solution is identified based on a difference between the measured average voltages $V_{ION-AVE}$ and $V_{REF-AVE}$.

According to different embodiments of this aspect of the invention, pH measurement may be accomplished simultaneously with conductivity measurement, or during mutually exclusive cycles.

DETAILED DESCRIPTION OF THE PREFERRED EMBODIMENTS

Figure 1:
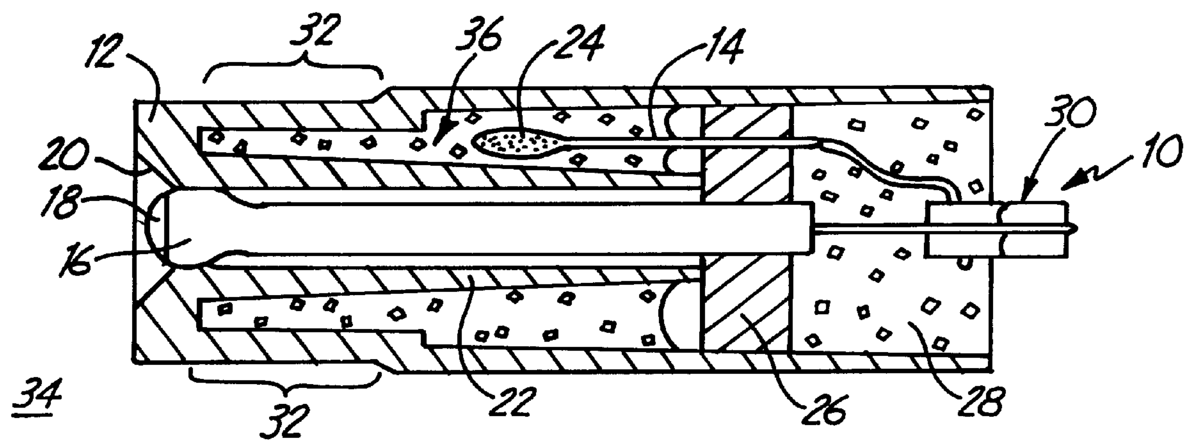
FIG. 1 is a section view of a typical ion-sensitive sensor as might be used in carrying out the present invention.

FIG. 1 illustrates a typical ion-sensitive sensor 10 as used in the present invention. More particularly, the sensor illustrated in FIG. 1 is described in U.S. Pat. No. (5,152,882, granted Oct. 6, 1992, for "Integral Hydrolysis Layer Junction", by Barry W. Benton and assigned to the same Assignee as the present invention. Ion-sensitive sensor 10 includes a housing 12 containing a reference half cell 14 and an indicating or ion-specific electrode 16. Electrode 16 includes a distal tip 18 that is exposed to sample solution 34 through opening 20 in the end of housing 12. Electrode 16 is preferably formed of an ion-sensitive insulating glass. Tip 18 of electrode 16 contains an ion-specific fill solution having a known pH. The influence of the solution inside the glass tip 18 versus the influence of the sample solution 34 on the outside of the glass gives rise to a measurable potential based on the hydrogen ($H^+$) or hydroxyl ($O^-$) ion content, and hence pH, of sample solution 34. Electrode 16 is commonly referred to as a glass electrode (due to its construction) or more generically as an ion-specific electrode.

Reference half cell 14 is electrically insulated from the ion-specific electrode 16 by an inner wall 22 of housing 12. Wall 22 is generally cylindrical in configuration to surround electrode 16, except for the active region at tip 18. The reference half cell includes a reference electrode 24 in electrical contact with the ion-specific electrode through sample solution 34. More particularly, reference electrode 24 is coupled through junction 32 of the sensor to sample solution 34. Optionally, an electrolyte 36 may couple reference electrode 24 to junction 32, in the manner taught by the aforementioned Benton patent. The reference electrode is designed to maintain a constant potential at any given temperature and serves to complete the pH measurement circuit within the solution. The reference electrode provides a known reference potential for the ion-specific electrode. The difference in the potentials of the ion-specific electrode and the reference electrodes provides a measurable signal proportional to pH.

Sensor 10 is sealed by a plug 26 and potting material 28, both as well known in the art. Coupler 30 separately connects half cell 14 and electrode 16 to a measurement circuit (not shown in FIG. 1).

Figure 2:
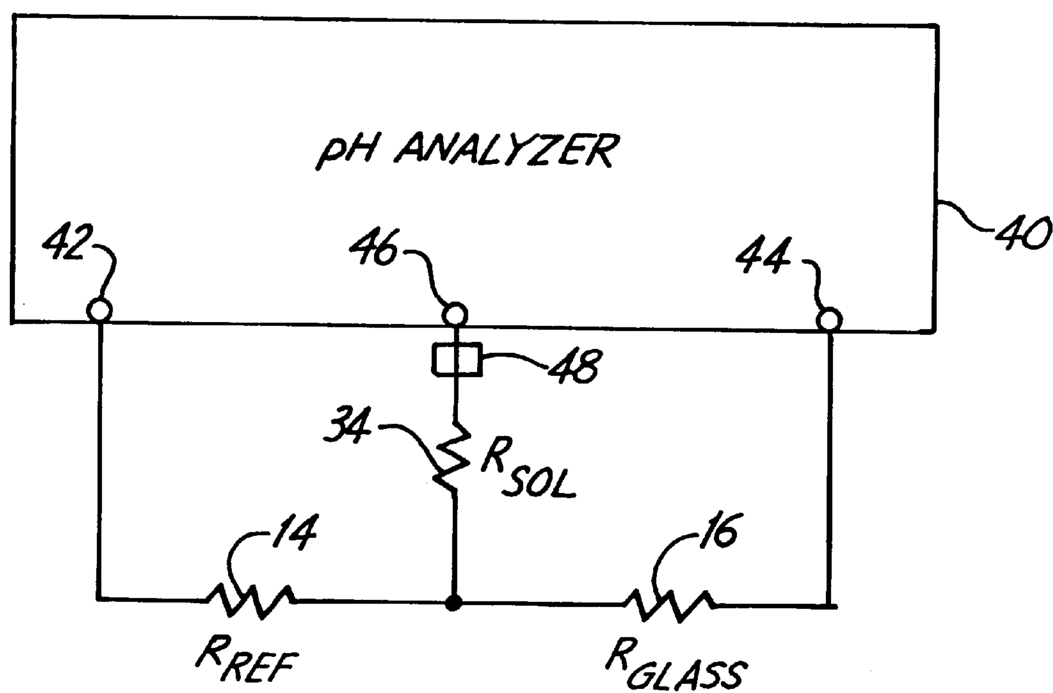
FIG. 2 is a schematic diagram illustrating the resistance circuit of an ion-sensitive sensor in a sample solution, as coupled to an analyzer.

FIG. 2 is a circuit diagram illustrating the equivalent circuit of ion-sensitive sensor 10, such as that illustrated in FIG. 1, connected to a pH analyzer 40. Analyzer 40 includes terminals 42 and 44 arranged to be coupled through coupler 30 of sensor 10 (FIG. 1) to the reference electrode 14 and ion-specific electrode 16, respectively. Analyzer 40 couples a third terminal 46 to a common electrical potential, such as electrical ground. Terminal 46 is coupled through an electrode 48 which is exposed to sample solution 34.

The operation of analyzer 40 to measure pH of solution 34 is described in U.S. Pat. No. 5,469,070 granted Nov. 21, 1995 to Roland H. Koluvek for "Circuit for Measuring Source Resistance of a Sensor". Current is applied to both the reference electrode input terminal 42 ($I_{REF}$) and the ion-specific electrode input terminal 44 ($I_{ION}$). $I_{REF}$ is a substantially constant (DC) current that alternates, or switches, between positive and negative states of equal or equivalent values, $I_{REF+}$, and $I_{REF-}$. The currents of $I_{REF+}$ and $I_{REF-}$ produce respective positive ($V_{REF+}$) and negative ($V_{REF-}$) peak voltages between terminals 42 and 46 (across reference electrode 14 and the sample solution 34). Similarly, $I_{ION}$ is a substantially constant (DC) current that alternates, or switches, between positive and negative states of equal or equivalent values, $I_{ION+}$ and $I_{ION-}$. The currents of $I_{ION+}$ and $I_{ION-}$ produce respective positive ($V_{ION+}$) and negative ($V_{ION-}$) peak voltages between terminals 44 and 46 (ion-specific electrode 16 and the sample solution 34). The peak voltages, $I_{ION+}$ and $I_{ION-}$, across terminals 42 and 46 are measured, and the average voltage, $V_{REF-AVE}$, across reference electrode 14 and the sample solution 34 is calculated. For example, it the voltage, $V_{REF}$, across terminals 42 and 46 alternates between peak voltages of +100 millivolts ($V_{REF+}$=100 mv) and −80 millivolts ($V_{REF-}$=−80 mv), the average voltage ($V_{REF-AVE}$) is +10 millivolts $$\left(V_{REF-AVE} = \frac{V_{REF+} + V_{REF-}}{2}\right).$$

Similarly, the peak voltages across terminals 44 and 46 ($V_{ION+}$ and $V_{ION-}$) are measured, and the average voltage, $V_{ION-AVE}$, is calculated. The difference between the two average voltage measurements is a measure of pH.

It will be appreciated that the average currents are zero. More particularly, since the values of $I_{REF+}$ and $I_{REF-}$ are equal and opposite, and the values of $I_{ION+}$ and $I_{ION-}$ are equal and opposite, the average reference electrode current $I_{REF-AVE}$ and the average ion-specific electrode current $I_{ION-AVE}$ are both zero ($I_{REF-AVE}=(I_{REF+}+I_{REF-})/2=0$ and $I_{ION-AVE}=(I_{ION+}+I_{ION-})/2=0$).

In accordance with the present invention, conductivity may be also measured using analyzer 40 and ion-sensitive sensor 10. The peak-to-peak voltage, $V_{ION-PEAK}$, across terminals 44 and 46 (ion-specific electrode 16 and solution 34) is calculated as the difference between the peak voltages ($V_{ION+}-V_{ION-}$). For example, if the voltage, $V_{ION}$, across terminals 44 and 46 alternates between peak voltages of +100 millivolts ($V_{ION+}$=100 mv) and −80 millivolts ($V_{ION-}$=−80 mv), the peak voltage ($V_{ION-PEAK}$) is 180 millivolts. The impedance of the solution, $R_{SOL}$, is computed from the peak-to-peak voltage, $V_{ION-PEAK}$, across terminals 44 and 46, and the peak-to-peak value of the applied current, $I_{REF-PEAK}$:

$$R_{SOL} = \frac{V_{ION-PEAK}}{I_{REF-PEAK}}.$$

The conductivity of the solution, $C_{SOL}$, is proportional to the inverse of the resistance:

$$C_{SOL} = \frac{I_{REF-PEAK}}{V_{ION-PEAK}}.$$

The peak values of the reference electrode current ($I_{REF}$) are equal and opposite ($I_{REF+}=-I_{REF-}$). Consequently, the peak-to-peak value of $I_{REF-PEAK}$ is twice the positive ($I_{REF+}$) or negative ($I_{REF-}$) peak value of $I_{REF}$, e.g., $I_{REF-PEAK}=2I_{REF+}$.

The present invention thus provides a simple technique for using the existing pH analyzer and ion-sensitive sensor for measuring conductivity of a sample solution. Conductivity and pH may be measured during the same or separate cycles such that the analyzer and sensor measure solution pH and solution conductivity substantially simultaneously during one cycle of $I_{REF}$ and $I_{ION}$, or during mutually exclusive cycles of $I_{REF}$ and $I_{ION}$. Additionally, the reference electrode current and ion-specific current may be used for calibration or diagnostic, and may be multiplexed to minimize noise as described in application Ser. No. 09/748,881 filed Dec. 27, 2000 by Behzad Rezvani for "Process for Minimizing Cross-talk in Diagnostic Signals of a pH Sensor" and assigned to the same assignee as the present invention.

While the present disclosure has characterized the ion-sensitive sensor as containing a reference electrode and an ion-specific electrode, the ion-specific electrode is not necessarily constructed of glass, and may be any suitable material. Hence, the term "glass" is not limiting on the construction of the ion-specific electrode.

Although the present invention has been described with reference to preferred embodiments, workers skilled in the art will recognize that changes may be made in form and detail without departing from the spirit and scope of the invention.

What is claimed is:

1. A process of measuring conductivity of a solution comprising steps of:

a) coupling a common electrode and an ion-sensitive sensor to an analyzer, the ion-sensitive sensor having an ion-specific electrode and a reference electrode, the ion-specific electrode being designed to provide an electrical potential based on the pH of the solution, the reference electrode being designed to be coupled to the ion-specific electrode through the solution to provide a reference electrical potential;

b) applying the ion-sensitive sensor and a common electrode to the solution; and c) operating the analyzer to perform steps of:

i) applying an alternating current having a peak-to-peak value, $I_{REF-PEAK}$, to the reference electrode, ii) measuring a peak voltage, $V_{ION-PEAK}$, between the ion-specific electrode and the common electrode, and iii) identifying the conductivity of the solution based on the relationship $$C_{SOL} = \frac{I_{REF-PEAK}}{V_{ION-PEAK}}.$$

2. The process of claim 1, wherein the current has first and second peaks of substantially constant DC value.

3. The process of claim 2, wherein the first and second peaks of the current are equal and opposite, and the peak-to-peak value of the current is the sum of the absolute values of the first and second peaks.

4. The process of claim 2, further including operating the pH analyzer to perform steps of:

iv) measuring an average voltage, $V_{ION-AVE}$, between the ion-specific electrode and the common electrode, v) measuring an average voltage, $V_{REF-AVE}$, between the reference electrode and the common electrode, and vi) identifying a difference between $V_{ION-AVE}$ and $V_{REF-Ave}$ as representative of pH of the solution.

5. The process of claim 4, wherein steps (i), (ii), (iv) and (v) are performed substantially simultaneously, and steps (iii) and (vi) are performed substantially simultaneously.

6. The process of claim 4, wherein steps (iii) and (vi) are performed during mutually exclusive cycles.

7. The process of claim 1, further including operating the pH analyzer to perform steps of:

iv) measuring an average voltage, $V_{ION-AVE}$, between the ion-specific electrode and the common electrode, v) measuring an average voltage, $V_{REF-AVE}$, between the reference electrode and the common electrode, and vi) identifying a difference between $V_{ION-AVE}$ and $V_{REF-AVE}$ as representative of pH of the solution.

8. The process of claim 7, wherein steps (i), (ii), (iv) and (v) are performed substantially simultaneously, and steps (iii) and (vi) are performed substantially simultaneously.

9. The process of claim 7, wherein steps (iii) and (vi) are performed during mutually exclusive cycles.

10. A process of operating a pH analyzer to measure conductivity of a solution, wherein a common electrode and an ion-sensitive sensor are coupled to the pH analyzer, the ion-sensitive sensor has an ion-specific electrode in contact with the solution to provide an electrical potential based on the pH of the solution, the ion-sensitive sensor further has a reference electrode coupled to the ion-specific electrode through the solution to provide a reference electrical potential, and the common electrode is coupled to the solution, the process comprising steps of:

a) applying a current having a peak value, $I_{REF-PEAK}$, to the reference electrode, b) measuring a peak voltage, $V_{ION-PEAK}$, between the ion-specific electrode and the common electrode, and c) identifying the conductivity of the solution based on the relationship $$C_{SOL} = \frac{I_{REF-PEAK}}{V_{ION-PEAK}}.$$

11. The process of claim 10, wherein the current has first and second peaks of substantially constant DC value.

12. The process of claim 11, wherein the first and second peaks of the current are equal and opposite, and the peak-to-peak value of the current is the sum of the absolute values of the first and second peaks.

13. The process of claim 11, further including measuring the pH of the solution by steps of:

d) measuring an average voltage, $V_{ION-AVE}$, between the ion-specific electrode and the common electrode, e) measuring an average voltage, $V_{REF-AVE}$, between the reference electrode and the common electrode, and f) identifying a difference between $V_{ION-AVE}$ and $V_{REF-AVE}$ as representative of pH of the solution.

14. The process of claim 13, wherein steps (a), (b), (d) and (e) are performed substantially simultaneously, and steps (c) and (f) are performed substantially simultaneously.

15. The process of claim 13, wherein steps (c) and (f) are performed during mutually exclusive cycles.

16. The process of claim 10, further including measuring the pH of the solution by steps of:

d) measuring an average voltage, $V_{ION-AVE}$, between the ion-specific electrode and the common electrode, e) measuring an average voltage, $V_{REF-AVE}$, between the reference electrode and the common electrode, and f) identifying a difference between $V_{ION-AVE}$ and $V_{REF-AVE}$ as representative of pH of the solution.

17. The process of claim 16, wherein steps (a), (b), (d) and (e) are performed substantially simultaneously, and steps (c) and (f) are performed substantially simultaneously.

18. The process of claim 16, wherein steps (c) and (f) are performed during mutually exclusive cycles.

19. A process of measuring conductivity of a solution, comprising steps of:

a) coupling a common electrode and an ion-sensitive sensor to a pH analyzer, the ion-sensitive sensor having an ion-specific electrode and a reference electrode, the ion-specific electrode being designed to provide an electrical potential based on the pH of the solution, the reference electrode being designed for coupling to the ion-specific electrode through the solution to provide a reference electrical potential;

b) applying the ion-sensitive sensor and the common electrode to the solution;

c) operating the pH analyzer to perform steps of;

c1) applying a first current, $I_{ION-PEAK}$, having first, $I_{ION+}$, and second, $I_{ION-}$, equal and opposite peak values, to the ion-specific electrode, c2) applying a second current, $I_{REF-PEAK}$, having third, $I_{REF+}$, and fourth, $I_{REF-}$, peak values to the reference electrode, c3) measuring a first, $V_{ION+}$, and second, $V_{ION-}$, peak voltage, between the ion-specific electrode and the common electrode, c4) calculating a peak voltage, $V_{ION-PEAK}$ based on a difference between the first and second peak voltages, and c5) identifying the conductivity of the solution based on the relationship $$C_{SOL} = \frac{I_{REF-PEAK}}{V_{ION-PEAK}},$$

where $V_{ION-PEAK}$ is the peak-to-peak voltage of $V_{ION-AVE}$.

20. The process of claim 19, wherein the pH analyzer is further operated to perform steps of:

c6) measuring a third, $V_{REF+}$, and fourth, $V_{REF-}$, peak voltage between the reference electrode and the common electrode, c7) calculating an average voltage, $V_{ION-AVE}$, based on the first and second peak voltages, c8) calculating an average voltage, $V_{REF-AVE}$, based on the third and fourth peak voltages, and c9) identifying the pH of the solution based on a difference between voltages $V_{ION-AVE}$ and $V_{REF-AVE}$.

* * * * *

UNITED STATES PATENT AND TRADEMARK OFFICE

CERTIFICATE OF CORRECTION

PATENT NO. : 6,498,492 B1
DATED : December 24, 2002
INVENTOR(S) : Rezvani

It is certified that error appears in the above-identified patent and that said Letters Patent is hereby corrected as shown below:

Column 4,
Line 64, "$V_{REF\text{-}Ave}$" should be -- $V_{REF\text{-}AVE}$ --

Signed and Sealed this

Eleventh Day of March, 2003

JAMES E. ROGAN
*Director of the United States Patent and Trademark Office*